US008748779B2

(12) United States Patent
Zhao et al.

(10) Patent No.: US 8,748,779 B2
(45) Date of Patent: Jun. 10, 2014

(54) METHOD AND APPARATUS FOR HEATING COUPLING MEDIUM

(75) Inventors: Zhensong Zhao, Wuxi (CN); Youfeng Teng, Wuxi (CN); Dongmei Li, Wuxi (CN); Quan Li, Wuxi (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 710 days.

(21) Appl. No.: 12/981,809

(22) Filed: Dec. 30, 2010

(65) Prior Publication Data

US 2011/0155362 A1 Jun. 30, 2011

(30) Foreign Application Priority Data

Dec. 30, 2009 (CN) .......................... 2009 1 0206776

(51) Int. Cl.
*F28F 7/00* (2006.01)
*A61B 8/00* (2006.01)
*H05B 1/00* (2006.01)
*H05B 3/00* (2006.01)

(52) U.S. Cl.
USPC .......... 219/209; 219/530; 165/185; 361/702; 361/703; 361/714

(58) Field of Classification Search
None
See application file for complete search history.

(56) References Cited

U.S. PATENT DOCUMENTS

| 5,568,810 | A |   | 10/1996 | Hamers et al. |
| 5,764,482 | A | * | 6/1998 | Meyer et al. ................... 361/699 |
| 5,838,065 | A | * | 11/1998 | Hamburgen et al. ......... 257/722 |
| 5,988,266 | A | * | 11/1999 | Smith et al. ..................... 165/78 |
| 6,026,888 | A | * | 2/2000 | Moore .......................... 165/80.3 |
| 6,253,836 | B1 | * | 7/2001 | Mitchell ......................... 165/86 |
| 6,301,107 | B1 | * | 10/2001 | Lev et al. ................. 361/679.52 |
| 6,400,565 | B1 | * | 6/2002 | Shabbir et al. ........... 361/679.54 |
| 6,575,906 | B1 |   | 6/2003 | Schembri, Jr. et al. |
| 6,708,754 | B2 | * | 3/2004 | Wei ................................... 165/46 |
| 6,958,915 | B2 | * | 10/2005 | Wang et al. .................... 361/709 |
| 6,980,419 | B2 |   | 12/2005 | Smith et al. |
| 7,352,570 | B2 |   | 4/2008 | Smith et al. |
| 8,016,927 | B2 | * | 9/2011 | Tracy et al. ..................... 96/420 |
| 2004/0130869 | A1 | * | 7/2004 | Fleck et al. ................... 361/687 |
| 2005/0168941 | A1 | * | 8/2005 | Sokol et al. .................. 361/688 |
| 2006/0082966 | A1 | * | 4/2006 | Lev et al. ...................... 361/687 |
| 2012/0085784 | A1 | * | 4/2012 | Bakris ........................ 222/146.2 |

FOREIGN PATENT DOCUMENTS

CN 101166472 A 4/2008
CN 201055384 Y 5/2008

OTHER PUBLICATIONS

Unofficial translation of SIPO Office Action for CN Application No. 200910206776.8 dated Jan. 26, 2014.

* cited by examiner

*Primary Examiner* — Joseph M Pelham
(74) *Attorney, Agent, or Firm* — Armstrong Teasdale LLP

(57) ABSTRACT

An ultrasound diagnostic apparatus includes an apparatus for heating a coupling medium, wherein the apparatus includes an external heat conductive unit, including a base for positioning a container storing the coupling medium, and an internal heat sink unit for absorbing heat from the heat generating unit of the ultrasound diagnostic apparatus. The external heat conductive unit and the internal heat sink unit are configured as separate assembly structures such that, in the state of assembly, the heat of the heat generating unit is transferred to the container through them.

15 Claims, 2 Drawing Sheets

US 8,748,779 B2

METHOD AND APPARATUS FOR HEATING COUPLING MEDIUM

CROSS REFERENCE TO RELATED APPLICATIONS

This application claims the benefit of Chinese Patent Application No. 200910206776.8 filed Dec. 30, 2009, which is hereby incorporated by reference in its entirety.

BACKGROUND OF THE INVENTION

This invention relates to an ultrasound imaging apparatus, in particular relates to a method and apparatus for heating a coupling medium and an ultrasound diagnostic apparatus including the apparatus for heating a coupling medium.

Ultrasound diagnostic professionals use a kind of substance called a "coupling medium" to enhance transmission of the ultrasound waves between transducer and examined patient. This medium is usually an aqueous gel stored in a container and is applied liberally to the skin area of the examined patient where the transducer will be in contact. For the patient to feel comfortable, the temperature of the gel should be close to the body temperature. Thus, heating apparatus can be used to heat the gel in the container.

U.S. Pat. No. 6,575,906 discloses a rapid-heating ultrasound gel warmer. An ultrasonic imaging system carries a holder that holds a container for storing a gel. The container includes a metallic cap including a heat exchanger in good thermal contact with the gel of the container, and the holder includes a heating element in good thermal contact with the metallic cap. When the ultrasound system is powered on, the power is applied to the heating element, thereby heating the gel in the container.

However, the prior heating methods consume certain power, although this is not a problem for cart type ultrasound imaging system because it is powered by AC power. But for portable ultrasound medical diagnostic imaging apparatus powered by batteries, the impact by heating the gel on energy consumption becomes remarkable.

It would be desirable then to provide a method and apparatus for heating a coupling medium that energy consumption required for heating can be saved and an ultrasound diagnostic apparatus including the apparatus for heating a coupling medium.

BRIEF DESCRIPTION OF THE INVENTION

It is an object of the present invention to provide a method and apparatus for heating a coupling medium and an ultrasound diagnostic apparatus which can notably save energy consumption required for heating.

In accordance with another aspect of the present invention, the apparatus for heating a coupling medium includes an external heat conductive unit, including a base for placing a container storing the coupling medium, and an internal heat sink unit for absorbing heat from the heat generating unit of the ultrasound diagnostic apparatus, wherein the external heat conductive unit and the internal heat sink unit are configured as separate assembly structures and, in the state of assembly, the heat of the heat generating unit is transferred to the container through them.

According to yet another aspect of the present invention, the ultrasound diagnostic apparatus includes an apparatus for heating a coupling medium including an external heat conductive unit, including a base for placing a container storing the coupling medium, and an internal heat sink unit for absorbing heat from the heat generating unit of the ultrasound diagnostic apparatus, wherein the external heat conductive unit and the internal heat sink unit are configured as separate assembly structures and, in the state of assembly, the heat of the heat generating unit is transferred to the container through them.

According to the preferred embodiments of this invention, since the heat generated during the operating process of the ultrasound diagnostic apparatus is utilized for heating the coupling medium, no extra energy can be consumed. On the other hand, the heat generated by the ultrasound diagnostic apparatus can be transferred to the coupling medium, the heat dissipation need of the ultrasound diagnostic apparatus can be satisfied.

BRIEF DESCRIPTION OF THE DRAWINGS

Reference is made to the following description of best embodiments in conjunction with the drawings, so as to a better understanding of the disclosure of the present invention.

FIGS. 1 and 2 are schematic views of a gel heating apparatus according to a preferred embodiment of the present invention, wherein FIG. 1 is an exploded view and FIG. 2 is a view of the assembly apparatus.

DETAILED DESCRIPTION OF THE INVENTION

Figure 1:
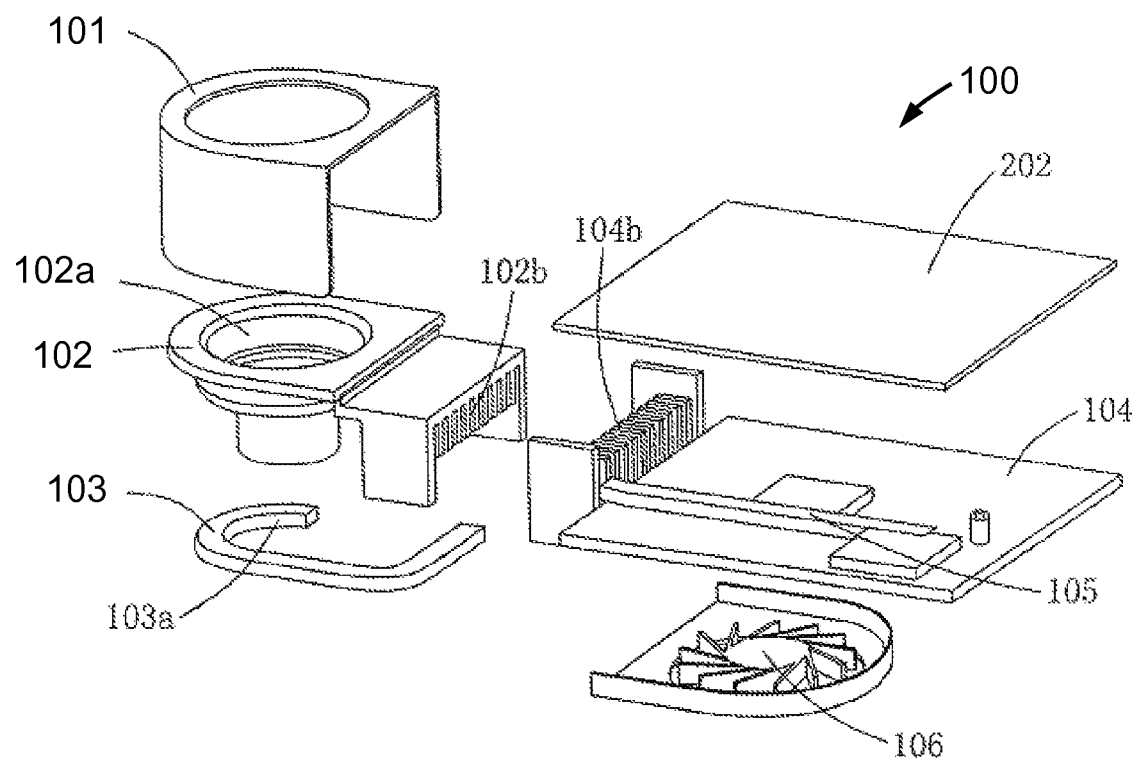

Reference is made to some specific embodiments of the present invention in detail below which include the modes regarded by the inventor as best embodiments for carrying out the invention. These particular embodiments will be illustrated in the drawings. When the present invention is described in combination with the particular embodiments, it is understood that it is not intended to limit the present invention to the described embodiments. Instead, it is intended to cover the replacements, modifications and variations that can be included within the spirit and scope of the invention as defined in the claims.

It should be noted in the following descriptions that the connection between two units does not mean that it must be direct. Unless specially explained, the term also covers the cases of the indirect connections through other units. For the word "contact", it includes both the cases of the direct contact between the respective portions of two units and the cases of the indirect contact formed through other units, unless otherwise explained.

Figure 2:
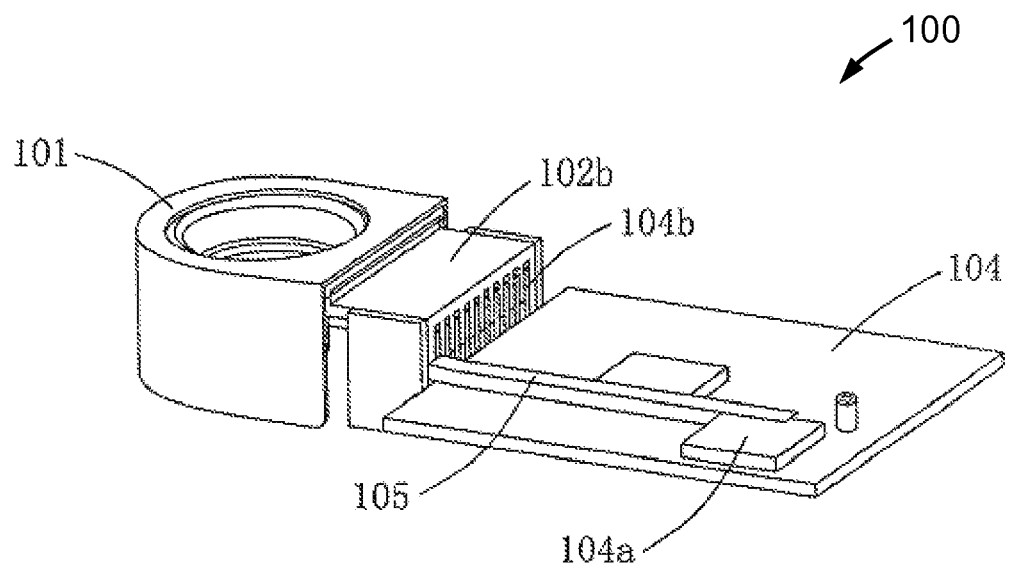

FIGS. 1 and 2 are schematic views of an apparatus for heating a coupling medium according to a preferred embodiment of the present invention. A gel heating apparatus 100 as shown in FIGS. 1 and 2 includes a case 101, a base 102, a first heat conductive pipe 103, a heat conductor 104, a second heat conductive pipe 105 and a fan 106.

As shown in the figures, the case 101 encloses the base 102 and the first heat conductive 103 to prevent operators from careless burns. The base 102 includes an inside recess region 102a for holding the container storing the gel (e.g. in the form of a bottle, not shown). The side of the base 102 is configured with at least one set of fins 102b for performing sufficient heat exchange with the heat conductor 104. One end of the first heat conductive pipe 103 includes an arc segment 103a, which at least partially encircles the bottom of the inside recess region 102a. When the base 102 is attached to the native machine of the ultrasound diagnostic apparatus, the other end of the first heat conductive pipe 103 may be in contact with the outside surface of the second heat conductive pipe 105 (for example, the other end of the first heat conductive pipe 103 is superimposed on the second heat conductive pipe 105) to transmit heat into the base 102. Especially, air in the first heat conductive pipe 103 may be pumped out and a certain amount of mediums may be injected, and then the pipe housing is sealed. In this way, the heat from the second heat conductive pipe 103 is inputted from the contact region to evaporate the mediums by absorbing heat into vapor, and the vapor flows to the arc segment 103a of the first heat conductive pipe 103, then condenses to release vapourization latent heat, and then flows back to the contact region. By such circulation, continuous heating of the container can be achieved. When used, the container can be located in the inside recess region 102a at an inverted position so as to make the gel near the container opening closer to the arc segment 103a of the first heat conductive pipe 103, thereby increasing the heating efficiency.

According to the preferred embodiment of this invention, the case 101, the base 102 and the first heat conductive pipe 103 are located outside the native machine of the ultrasound diagnostic apparatus (not shown), while the heat conductor 104, the second heat conductive pipe 105 and the fan 106 are mounted inside the ultrasound diagnostic apparatus. The specific positions of the heat conductor 104, the second heat conductive pipe 105 and the fan 106 may be determined dependent on the positions of the heat source or heat generating unit within the ultrasound diagnostic apparatus. For example, for a portable ultrasound medical imaging apparatus, the heat source thereof includes the elements with great heat generation like the processor chip, the image display chip and the display screen and so on. Thus, as shown in FIGS. 1 and 2, the heat conductor 104 is mounted adjacent to an electric unit 202 generating heat (e.g. a printed circuit board), preferably in contact with the elements with great heat generation like a chip on the electric unit 202. In this way, the heat generated when the elements are on operation can be highly efficiently transferred to the heat conductor 104. As illustrated by FIG. 2, a protrusion portion 104a is arranged at a position where the surface of the heat conductor 104 corresponds to the elements with great heat generation, to form the contact with the heat source. It is worth noting that the heat conductor 104 may be either in contact with the heat source or in a certain distance therefrom. These variations all fall within the protection scope of the present invention. The second heat conductive pipe 105 may be directly in contact with the heat source, or near the heat source. Preferably, as shown in FIG. 2, the second heat conductive pipe 105 is in contact with the protrusion portion 104a on the heat conductor 104. In another aspect, as mentioned above, when the base 102 is attached to the native machine of the ultrasound diagnostic apparatus, the second heat conductive pipe 105 and the first heat conductive pipe 103 form a face-contact to lead heat out of the ultrasound diagnostic apparatus so as to provide a high heat conducting efficiency. For the second heat conductive pipe 105, the same working principle can be utilized as the first heat conductive pipe 103.

With reference to FIGS. 1 and 2, the side of the heat conductor 104 is configured with an upper portion fin set 104b and a lower portion fin set (not drawn). The upper portion fin set 104b mates with the fin set 102b of the base 102 and they are in rather close contact. That is, one fin of one of the fin sets is between the two fins of the other fin set. Therefore, the heat exchange area between the base 102 and the heat conductor 104 are remarkably increased so that the heating effect is enhanced. Additionally, preferably, the side of the housing of the ultrasound diagnostic apparatus is provided with an opening, and the base 102, through the mating of the fin set 102b with the upper portion fin set 104b, is mounted at the opening in a detachable way. In this way, the base 102 can be detached from the host machine of the apparatus when there is no need to heat the gel, so that the portability and normal work of the apparatus are ensured.

It is worth noting that the heat transfer between the base 102 and the heat conductor 104 may be performed by other means. For example, the sides of the two are both flat so as to form the face-contact.

Under the high temperature ambient (e.g. 40° C.), the gel possibly requires no heating, i.e. can be directly applied. At this time, for solving the heat dissipation problem of the ultrasound diagnostic apparatus, the fan 106 can be mounted internally which transfers the heat of the heat source to the outside of the ultrasound diagnostic apparatus by air circulation. For instance, as shown in FIG. 1, the fan 106 is located at the bottom of the heat conductor 104, and the air flow produced thereby blows the heat generated by the heat source to the opening of the housing. Since there are spaces between the lower portion fins of the base 102 and which are not in contact with the fin set 102b, the air flow can still pass the lower portion fins and the opening of the housing so as to carry heat to the outside of the ultrasound diagnostic apparatus.

Figure 3:
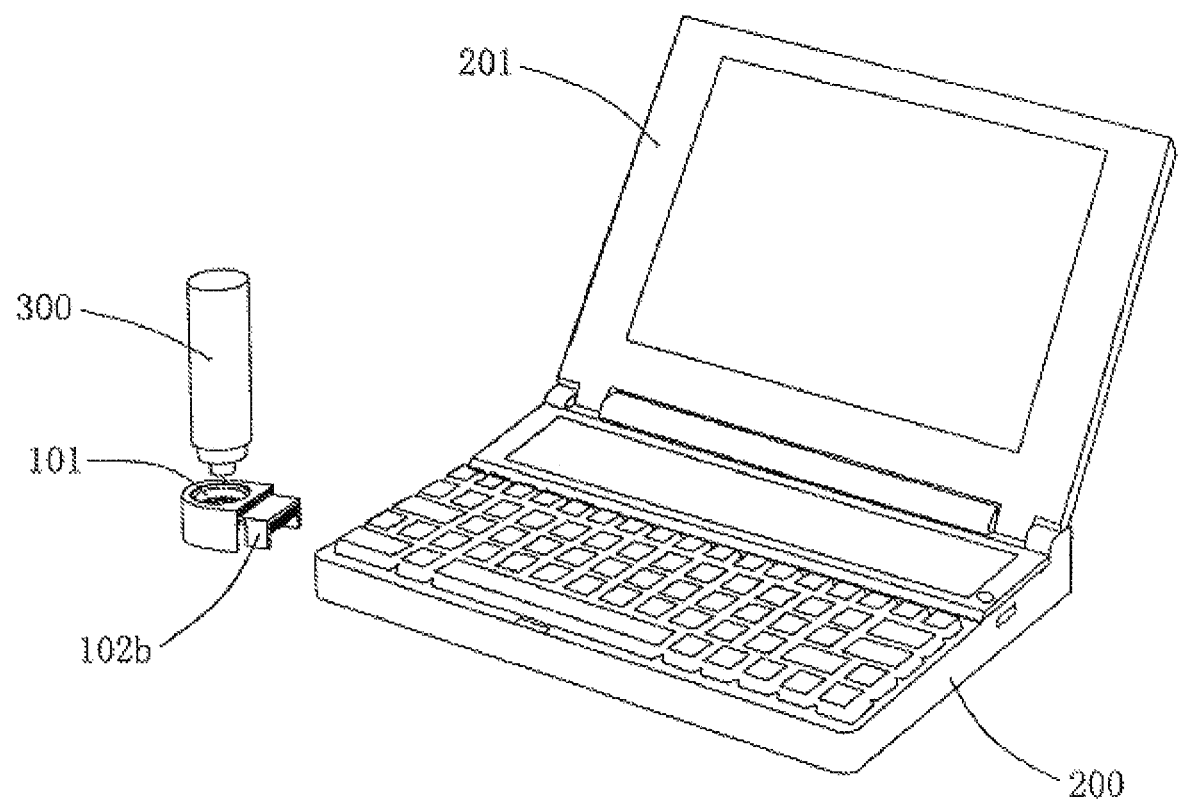
FIG. 3 is a schematic view of the ultrasound diagnostic apparatus according to another preferred embodiment of the present invention.

FIG. 3 is a schematic view of the ultrasound diagnostic apparatus according to one preferred embodiment of the present invention. An ultrasound diagnostic apparatus 200 is added with the gel heating apparatus 100 as shown in FIGS. 1 and 2 to the host machine thereof. The host machine herein refers to, e.g. units performing the ultrasound diagnostic function. Spatially, they are usually mounted inside a housing, e.g. a housing represented by reference number 201 in FIG. 3. As shown in FIG. 3, the base 102 and the first heat conductive pipe 103 are mounted in the case 101 and separate from the native machine 201 of the ultrasound diagnostic apparatus, while the other components of the gel heating apparatus 100 (such as the heat conductor 104, the second heat conductive pipe 105 and the fan 106) are located in the native machine 201 of the ultrasound diagnostic apparatus. If the gel in a container 300 requires heating, the base 102 can be plugged into the opening at the side of the native machine 201 of the ultrasound diagnostic apparatus and the container 300 is placed in the inside recess region 102a of the base 102.

Though the aforesaid invention is described in detail for the purpose of clear understanding, it is obvious that some variations and modifications may be made within the scope sought for protection by the appended claims. Thus, the embodiments are just illustrative, not limitative. Moreover, this invention is not limited by the given details, but can be modified with the equivalents within the scope of the appended claims.

What is claimed is:

1. A method for heating a coupling medium contained in a container, said method comprising:
    coupling the container to an ultrasound diagnostic apparatus;
    providing, in the ultrasound diagnostic apparatus, a heat conductor having at least a portion adjacent to a heat generating unit of the ultrasound diagnostic apparatus;
    providing a holder configured to hold the container outside of the ultrasound diagnostic apparatus, the heat conductor and the holder including sets of fins configured to mate with each other; and transferring heat generated by operation of the ultrasound diagnostic apparatus to the container for heating the coupling medium.

2. The method according to claim 1, wherein the holder includes a base detachably attached to the ultrasound diagnostic apparatus.

3. The method according to claim 1, wherein the container and the ultrasound diagnostic apparatus are coupled by heat conductive pipes.

4. The method according to claim 1, wherein the holder defines an inside recess portion for holding the container in an inverted position therein.

5. An apparatus for use in heating a coupling medium used for an ultrasound diagnostic apparatus, said apparatus comprising:
an external heat conductive unit comprising a base sized to hold a container storing the coupling medium; and
an internal heat sink unit configured to absorb heat from a heat generating unit of the ultrasound diagnostic apparatus, wherein said external heat conductive unit and said internal heat sink unit are configured as separable assembly structures such that, in the state of assembly, heat generated by the heat generating unit is transferred to the container through them, and wherein to facilitate heat exchange between said external heat conductive unit and said internal heat sink unit, said external heat conductive unit further comprises a first heat conductive pipe arranged in said base, said internal heat sink unit comprises a second heat conductive pipe arranged near the heat generating unit of the ultrasound diagnostic apparatus, and said first and second heat conductive pipes are configured to contact one another to transfer the heat of the heat generating unit through said base to the container.

6. The apparatus according to claim 5, wherein to facilitate heat exchange between said external heat conductive unit and said internal heat sink unit, said internal heat sink unit comprises a heat conductor in contact with the heat generating unit, and sets of fins configured to mate with each other are arranged on said base and said heat conductor to transfer the heat of said heat conductor through said base to the container.

7. The apparatus according to claim 6, wherein said internal heat sink unit comprises a fan having a wind current pathway that passes through said sets of fins.

8. The apparatus according to claim 5, wherein said base defines an inside recess portion sized to hold the container in an inverted position.

9. An ultrasound diagnostic apparatus, comprising:
a heat generating unit; and
an apparatus for heating a coupling medium, said apparatus comprising:
an external heat conductive unit comprising a base sized to hold a container storing the coupling medium; and
an internal heat sink unit configured to absorb heat from said heat generating unit, wherein said external heat conductive unit and said internal heat sink unit are configured as separable assembly structures such that, in the state of assembly, heat generated by said heat generating unit is transferred to the container through them, and wherein to facilitate heat exchange between said external heat conductive unit and said internal heat sink unit, said external heat conductive unit further comprises a first heat conductive pipe arranged in said base, said internal heat sink unit comprises a second heat conductive pipe arranged near the heat generating unit of the ultrasound diagnostic apparatus, and said first and second heat conductive pipes are configured to contact one another to transfer the heat of said heat generating unit through said base to the container.

10. The ultrasound diagnostic apparatus according to claim 9, wherein to facilitate heat exchange between said external heat conductive unit and said internal heat sink unit, said internal heat sink unit comprises a heat conductor in contact with said heat generating unit, and sets of fins configured to mate with each other are arranged on said base and said heat conductor to transfer the heat of said heat conductor through said base to the container.

11. The ultrasound diagnostic apparatus according to claim 9, wherein said base defines an inside recess portion sized to hold the container in an inverted position.

12. The ultrasound diagnostic apparatus according to claim 10, further comprising a fan having a wind current pathway that passes through said sets of fins.

13. The ultrasound diagnostic apparatus according to claim 9, wherein said base and said first heat conductive pipe are detachably attached to said internal heat sink unit.

14. The ultrasound diagnostic apparatus according to claim 9, wherein said ultrasound diagnostic apparatus is a portable ultrasound medical imaging apparatus.

15. The ultrasound diagnostic apparatus according to claim 10, wherein said ultrasound diagnostic apparatus is a portable ultrasound medical imaging apparatus.

* * * * *